United States Patent
Sim

(10) Patent No.: US 10,768,171 B2
(45) Date of Patent: Sep. 8, 2020

(54) DISPOSABLE TEST KIT

(71) Applicant: Cell ID Pte Ltd, Singapore (SG)

(72) Inventor: Lye Hock Sim, Singapore (SG)

(73) Assignee: CELL ID PTE LTD, Singapore (SG)

( * ) Notice: Subject to any disclaimer, the term of this patent is extended or adjusted under 35 U.S.C. 154(b) by 91 days.

(21) Appl. No.: 15/557,069

(22) PCT Filed: Mar. 10, 2015

(86) PCT No.: PCT/SG2015/000069
§ 371 (c)(1),
(2) Date: Sep. 8, 2017

(87) PCT Pub. No.: WO2016/144252
PCT Pub. Date: Sep. 15, 2016

(65) Prior Publication Data
US 2018/0067106 A1    Mar. 8, 2018

(51) Int. Cl.
*G01N 33/558* (2006.01)
*G01N 33/52* (2006.01)
*G01N 21/84* (2006.01)

(52) U.S. Cl.
CPC ....... *G01N 33/521* (2013.01); *G01N 21/8483* (2013.01); *G01N 33/52* (2013.01); *G01N 33/558* (2013.01)

(58) Field of Classification Search
CPC .................................................. G01N 33/558
USPC ....... 422/401, 402, 408, 409, 420, 425, 430; 435/287.7, 287.9, 970; 436/514, 518, 436/530, 810
See application file for complete search history.

(56) References Cited

U.S. PATENT DOCUMENTS 4,328,184 A * 5/1982 Kondo ................. G01N 33/521
422/401
4,541,987 A * 9/1985 Guadagno ............ G01N 33/725
422/401

(Continued)

FOREIGN PATENT DOCUMENTS

CN    1217060 C    5/1999
CN    1948965 A    4/2007

(Continued)

OTHER PUBLICATIONS

Foreign Communication from a Related Counterpart Application, Office Action dated Feb. 20, 2019, China Application No. 201580079161.7.

(Continued)

*Primary Examiner* — Christopher L Chin

(57) ABSTRACT

A disposable test kit comprising a base sheet; a sealing sheet having at least one sealed sample collection opening before use of the test kit; at least one test strip sealed between the base sheet and the sealing sheet before use of the test kit; and at least one top sheet layered over the sealing sheet before use of the test kit to keep the at least one sample collection opening sealed, the at least one top sheet further configured to be at least partially detached from the sealing sheet to open the at least one sample collection opening and expose a sample collection portion of the at least one test strip for receiving a fluid analyte thereon during use of the test kit.

15 Claims, 5 Drawing Sheets

(56) References Cited

U.S. PATENT DOCUMENTS

| | | | | |
|---|---|---|---|---|
| 5,962,333 A | * | 10/1999 | Incorvia | B01L 3/5023 |
| | | | | 422/401 |
| 6,475,805 B1 | * | 11/2002 | Charm | G01N 33/537 |
| | | | | 422/110 |
| 2002/0076828 A1 | | 6/2002 | Kobayashi | |
| 2004/0191760 A1 | | 9/2004 | Zhou | |
| 2005/0123439 A1 | | 6/2005 | Patton et al. | |
| 2015/0056687 A1 | * | 2/2015 | Tyrrell | B01L 3/5023 |
| | | | | 435/287.2 |

FOREIGN PATENT DOCUMENTS

| | | |
|---|---|---|
| JP | 2-44212 Y2 | 11/1990 |
| JP | 2-306143 A | 12/1990 |
| JP | 5-21013 Y2 | 5/1993 |
| JP | 7-198706 A | 8/1995 |
| JP | 9-297139 A | 11/1997 |
| JP | 2006177968 A | 7/2006 |
| JP | 2008249657 A | 10/2008 |
| JP | 2010-107401 A | 5/2010 |
| JP | 2014-190926 A | 10/2014 |
| WO | 9742505 A1 | 11/1997 |
| WO | 2016144252 A1 | 9/2016 |

OTHER PUBLICATIONS

Foreign Communication from a Related Counterpart Application, Notification of Reasons for Refusal dated Dec. 12, 2018, Japan Application No. 2017-566603.

Foreign Communication From a Related Counterpart Application, International Search Report and Written Opinion dated Jun. 2, 2015, International Application No. PCT/SG2015/000069 filed on Mar. 10, 2015.

* cited by examiner

DISPOSABLE TEST KIT

CROSS-REFERENCE TO RELATED APPLICATIONS

The present application is a filing under 35 U.S.C. 371 as the National Stage of International Application No. PCT/SG2015/000069, filed Mar. 10, 2015, entitled "A DISPOSABLE TEST KIT," which is incorporated herein by reference in its entirety for all purposes.

FIELD OF THE INVENTION

This invention relates to a disposable test kit, and in particular, to a disposable test kit for conducting an immunoassay on a fluid analyte.

BACKGROUND OF THE INVENTION

Disposable test kits such as home pregnancy test kits or laboratory test kits using bodily fluids such as urine or blood to detect or diagnose disease or other medical conditions are in common use throughout the world. Such test kits typically comprise a test strip sealed in a moisture barrier packaging before use in order to keep the test strip stable and protected during storage and transportation, to extend the shelf life of the test kit. The moisture barrier packaging typically comprises a foil bag or pouch. The test strip may additionally be encased in a plastic cassette for easier handling by the end user, in which case the test strip and cassette are both sealed in the moisture barrier bag before use. Where the test kit includes a cassette, the cassette is typically provided with an open reaction window that allows one or more test lines on the test strip to be viewed during use. Depending on the method of fluid analyte collection that the test strip is designed for, the cassette is configured accordingly to allow a sample collection portion of the test strip to receive the fluid analyte either via a drop collection or dipstick/midstream collection method.

As disposable test kits are used in great quantities internationally, there is a need to provide them at as low a cost and as conveniently as possible, particularly in order to benefit those in impoverished circumstances. In epidemic situations, there is also a need to ensure that tests can be safely and effectively performed, and results effectively captured and stored.

SUMMARY OF INVENTION

According to a first aspect, there is provided a disposable test kit comprising a base sheet; a sealing sheet having at least one sealed sample collection opening before use of the test kit; at least one test strip sealed between the base sheet and the sealing sheet before use of the test kit; and at least one top sheet layered over the sealing sheet before use of the test kit to keep the at least one sample collection opening sealed, the at least one top sheet further configured to be at least partially detached from the sealing sheet to open the at least one sample collection opening and expose a sample collection portion of the at least one test strip for receiving a fluid analyte thereon during use of the test kit.

The at least one sample collection opening and the sample collection portion may be configured to allow the fluid analyte to be received by the sample collection portion via one of: a dipstick method, a drop method and a mid-stream collection method.

The sample collection opening may be sealed by a cover before use of the test kit, the cover being attached to the top sheet such that at least partially detaching the top sheet from the sealing sheet detaches the cover from the sealing sheet to open the sample collection opening.

The at least one test strip may be at least one of: a lateral flow test strip and a dipstick test strip.

The at least one test strip is at least one dipstick test strip and the sample collection portion comprises at least one test pad impregnated with a reagent. The sealing sheet may further comprise at least one transparent portion configured as a reaction window and wherein the at least one test strip is at least one lateral flow test strip having at least one test line viewable through the reaction window.

Alternatively, the at least one top sheet may further comprise at least one transparent portion aligned with the reaction window of the sealing sheet. The base sheet, the sealing sheet and the at least one top sheet may each comprise a moisture barrier polymeric film.

The test kit may require no additional moisture barrier packaging to keep the at least one test strip stable during storage of the test kit before use.

The test kit may comprise at least one quick response code provided thereon for storing information therein.

The at least one top sheet may be configured to be reattachable to the sealing sheet to cover the at least one sample collection opening after use of the test kit to prevent the fluid analyte on the sample collection portion from coming into contact with another object.

The at least one top sheet may comprise a first top sheet layered over the sealing sheet and configured to keep the sample collection opening sealed before use of the test kit, the first top sheet having a drop collection opening sealed before use of the test kit and a second top sheet layered over the first top sheet and configured to keep the drop collection opening sealed before use of the test kit, wherein the first top sheet is further configured to be at least partially detached from the sealing sheet to open the sample collection opening of the sealing sheet and expose the sample collection portion of the test strip for receiving a fluid analyte thereon via one of: a dipstick method and a mid-stream collection method during use of the test kit, and wherein the second top sheet is further configured to be at least partially detached from the first top sheet to open the drop collection opening on the first top sheet and expose the sample collection portion for receiving a fluid analyte thereon via a drop method during use of the test kit, thereby providing a user of the test kit with a choice of which of the first top sheet and the second top sheet to detach according to how the user prefers the fluid analyte to be received by the test kit.

The test kit may comprise a plurality of test panels each comprising a test strip having a sample collection portion and individually sealed between the base sheet and the sealing sheet before use of the test kit, the sealing sheet having a plurality of sealed sample collection openings before use of the test kit, each sample collection opening configured to be opened by at least partially detaching the at least one top sheet from the sealing sheet to expose each sample collection portion during use of the test kit.

The plurality of test panels may be configured to perform a different immunoassay.

The test kit may comprise at least one line of perforations provided therethrough and located between two adjacent test panels to allow at least one of the plurality of test panels to be manually separated from the test kit.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

DETAILED DESCRIPTION

Figure 1:
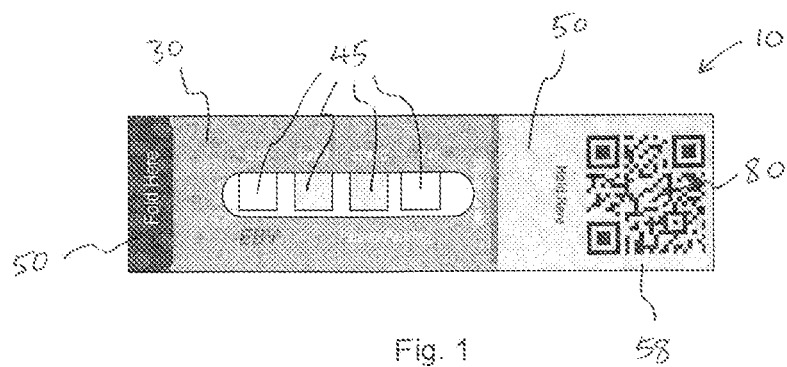
FIG. 1 is a top view of a first exemplary embodiment of a disposable test kit of the present invention with part of a top sheet detached from the test kit.

Exemplary embodiments of the disposable test kit 10 will be described below with reference to FIGS. 1 to 7. Same reference numerals are used throughout the figures to denote the same or similar parts of the test kit 10 among the different embodiments.

Figure 2:
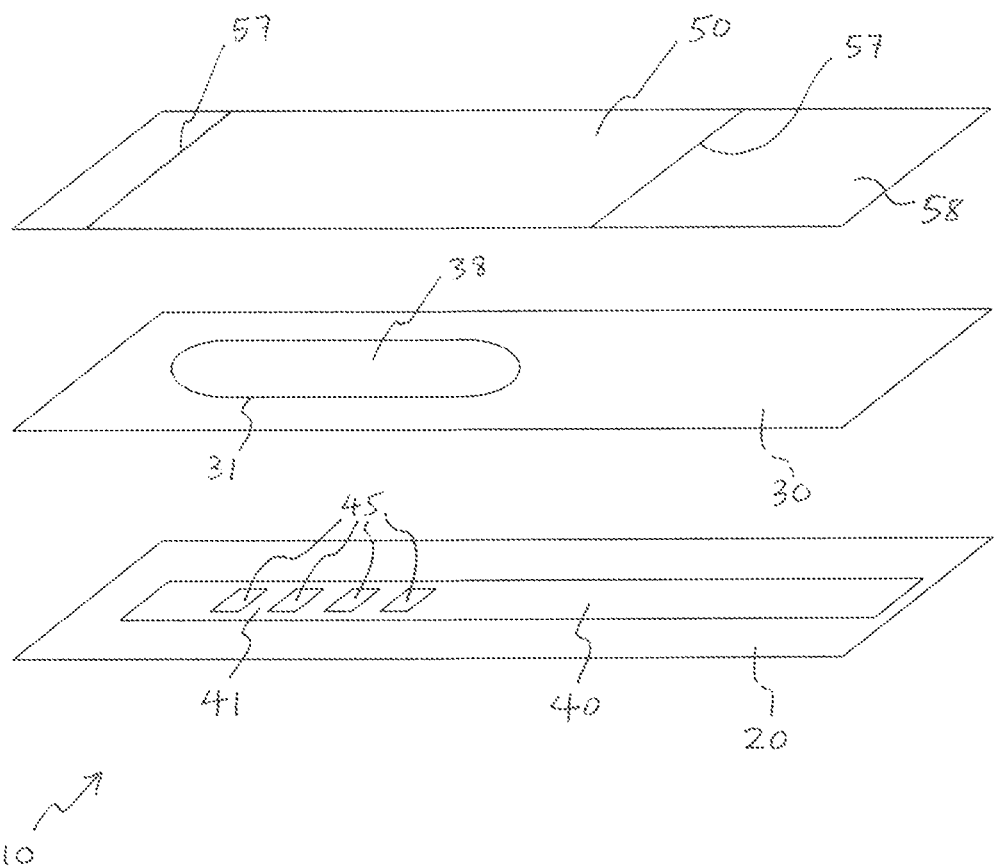
FIG. 2 is an exploded assembly illustration of the test kit of FIG. 1 before use.

As shown in FIGS. 1 and 2, in a first embodiment, the disposable test kit 10 is a dipstick test kit and comprises a base sheet 20, a sealing sheet 30 having a sealed sample collection 31 opening before use of the test kit 10, a dipstick test strip 40 sealed between the base sheet 20 and the sealing sheet 30 before use of the test kit 10, and a top sheet 50. The top sheet 50 is configured to be attached to the sealing sheet 30 before use of the test kit 10 to keep the sample collection opening 31 sealed. The base sheet 20, sealing sheet 30 and top sheet 50 are preferably rectilinear in shape and of the same size so that the disposable test kit 10 is a simple, almost flat rectangular package.

As shown in FIG. 2, the top sheet 50 is further configured to be at least partially detached from the sealing sheet 30 to open the sample collection opening 31 during use of the test kit 10. When the sample collection opening 31 has been opened, a sample collection portion 41 of the dipstick test strip 40 is exposed through the sample collection opening 31 and can then receive a fluid analyte thereon. This may be achieved by layering the top sheet 50 over the sealing sheet 30 and providing the top sheet 50 with appropriately located die cut lines 57 (e.g. on at least one side of the sample collection opening 31) to allow the top sheet 50 to be at least partially peeled away from the sealing sheet 30.

The sample collection opening 31 is preferably sealed by a cover 38 before use of the test kit 10. The cover 38 is attached to the top sheet 50 such that at least partially detaching the top sheet 50 from the sealing sheet 30 detaches the cover 38 from the sealing sheet 30 to open the sample collection opening 31. The cover 38 is preferably integral with or part of the sealing sheet 30 before use of the test kit 10.

The top sheet 50 is preferably also configured to be reattachable to the sealing sheet 30 to cover the sample collection opening 31 after use of the test kit 10, in order to prevent the fluid analyte on the sample collection portion 41 from coming into contact with another object. This is a safety or hygiene feature to minimize or prevent human handlers of the used test kit 10 from being contaminated by contaminants in the fluid analyte, and to minimize or prevent cross contamination with other used test kits 10.

As a dipstick test kit 10, the sample collection portion 41 comprises at least one test pad 45 impregnated with a suitable reagent for reacting with various compounds in the fluid analyte, which may be a urine sample, for example. The sample collection opening 31 and sample collection portion 41 are configured to allow a fluid analyte to be received by the sample collection portion 41 via a dipstick or mid-stream method once the sample collection opening 31 has been opened by detaching the top sheet 50.

Figure 3:
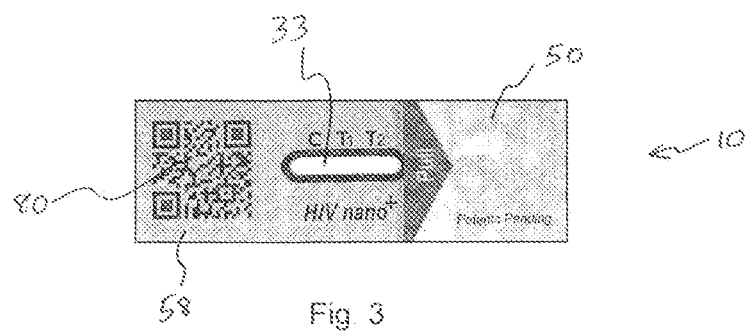
FIG. 3 is a top view of a second exemplary embodiment of a disposable test kit of the present invention.
Figure 4:
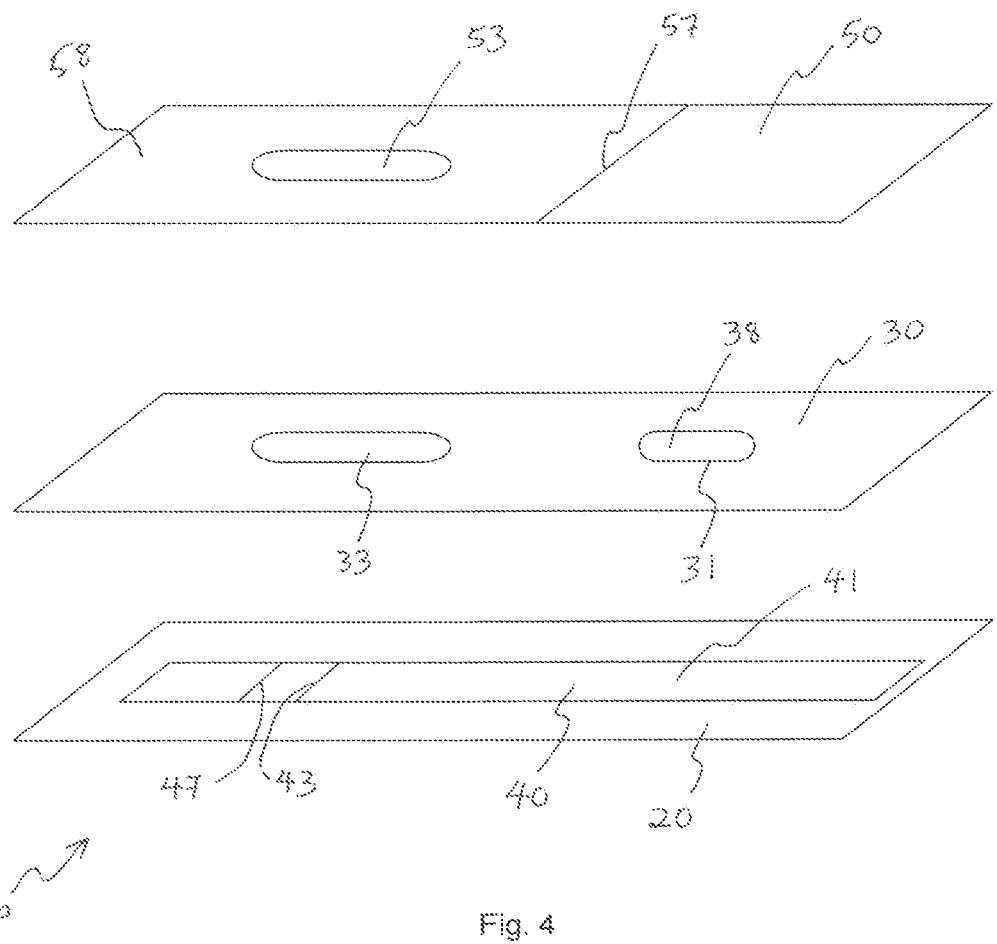
FIG. 4 is an exploded assembly illustration of the test kit of FIG. 3 before use.

In a second embodiment as shown in FIGS. 3 and 4, the test kit 10 is a lateral flow test kit, therefore the test strip 40 is a lateral flow test strip having at least one test line 43, and preferably also at least one control line 47. In this embodiment, the sealing sheet 30 is provided with a transparent portion configured as a reaction window 33 aligned over the test line 43 and the control line 47 so that they 43, 47, can be seen through the reaction window 33. In this embodiment, as the top sheet 50 is layered over all of the sealing sheet 30, the top sheet 50 also comprises a transparent portion 53 aligned with the reaction window 33 of the sealing sheet 30 to allow the test line 43 and the control line 47 to be seen through both the sealing sheet 30 and the top sheet 50 layers. In an alternative embodiment, the top sheet 50 may be layered only partially over the sealing sheet 30 without being layered over the reaction window 33, in which case no transparent portion needs to be provided in the top sheet 50.

Similar to the first embodiment, the second embodiment test kit also has a sample collection opening 31 in the sealing sheet 30 that is sealed before use of the test kit 10, and similarly opened by detaching the top sheet 50 from the sealing sheet 30.

The sample collection opening 31 and the sample collection portion 41 of the lateral flow test kit 10 are configured to allow the fluid analyte to be received by the sample collection portion 41 by various possible methods such as a dipstick method, a drop method and/or a mid-stream collection method depending on the type of fluid analyte to be collected and as already known in the art. For example, for an HIV test, the lateral flow test kit 10 will be configured to have the sample collection portion 41 receive blood via a drop method. As a pregnancy test, the lateral flow test kit 10 can be configured to have the sample collection portion 41 designed to collect urine via one or more of a drop collection, mid-stream collection or a dipstick method.

Figure 5:
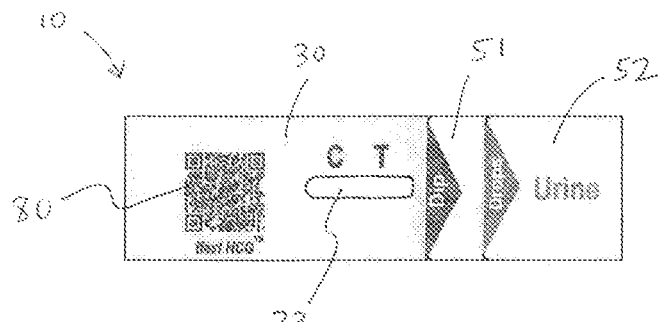
FIG. 5 is a top view of a third exemplary embodiment of a disposable test kit of the present invention.
Figure 6:
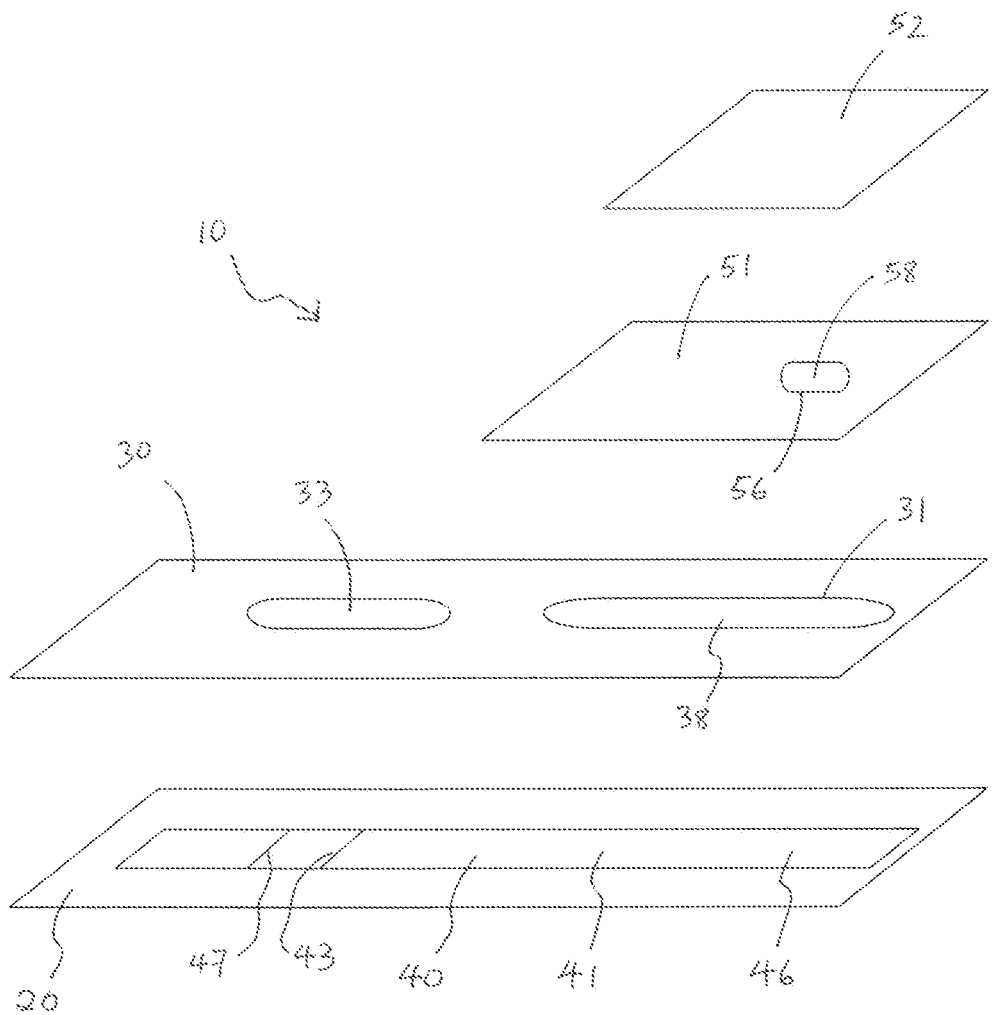
FIG. 6 is an exploded assembly illustration of the test kit of FIG. 5 before use.

In a third embodiment as shown in FIGS. 5 and 6, the test kit 10 is also a lateral flow test kit having a lateral flow test strip 40 and a reaction window 33, but configured to allow a user to select the sample collection method, i.e. via a dipstick or drop method. To that end, the sealing sheet 30 of the third embodiment is provided with two top sheets 51, 52. The first top sheet 51 is layered over the sealing sheet 30, and is configured to keep the sample collection opening sealed 31 before use of the test kit. The first top sheet 51 is additionally provided with a drop collection opening 56 that is sealed before use of the test kit 10. The drop collection opening 56 is located to be aligned over part 46 of the sample collection opening 31 of the sealing sheet 30. The second top sheet 52 is layered over the first top sheet 51, and is configured to keep the drop collection opening 56 on the first top sheet 51 sealed before use of the test kit 10. The drop collection opening 56 is preferably sealed by a cover 58 before use of the test kit 10.

Similar to the first embodiment, in the third embodiment, the first top sheet 51 is further configured to be at least partially detached from the sealing sheet 30 to open the sample collection opening 31 of the sealing sheet 30 and expose the sample collection portion 41 of the test strip 40 for receiving a fluid analyte thereon via one of: a dipstick method and a mid-stream collection method during use of the test kit 10.

The second top sheet 52 is configured to be at least partially detached from the first top sheet 51 to open the drop collection opening 56 on the first top sheet 51 and expose part 46 of the sample collection portion 41 for receiving a fluid analyte thereon via a drop method during use of the test kit 10.

In the third embodiment, detaching the first top sheet 51 from the sealing sheet 30 also means that the second top sheet 52 is detached from the test kit 10 at the same time, since the second top sheet 52 is layered over the first top sheet 51.

Since the test kit 10 of the third embodiment is a lateral flow test kit 10, it is preferably also provided with a transparent reaction window 33 in the sealing sheet 30 to allow the at least one test line 43 of the lateral flow test strip 40 to be viewed. The first top sheet 51 is only partially layered over the sealing sheet 30 without covering the reaction window 33 of the sealing sheet 30, so no transparent portion is provided in the first top sheet 51. Alternatively, if it is desired to layer the first top sheet 51 over all of the sealing sheet 30, the first top sheet 51 should accordingly be provided with a transparent portion 53 over the reaction window 33.

Figure 7:
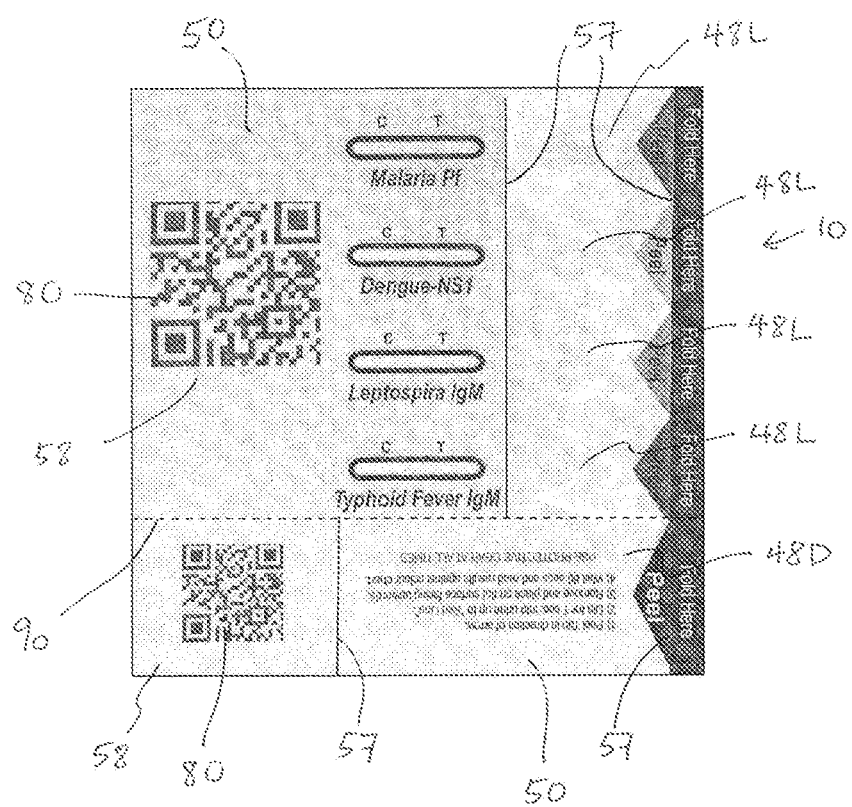
FIG. 7 is a top view of a fourth exemplary embodiment of a disposable test kit of the present invention.
Figure 8:
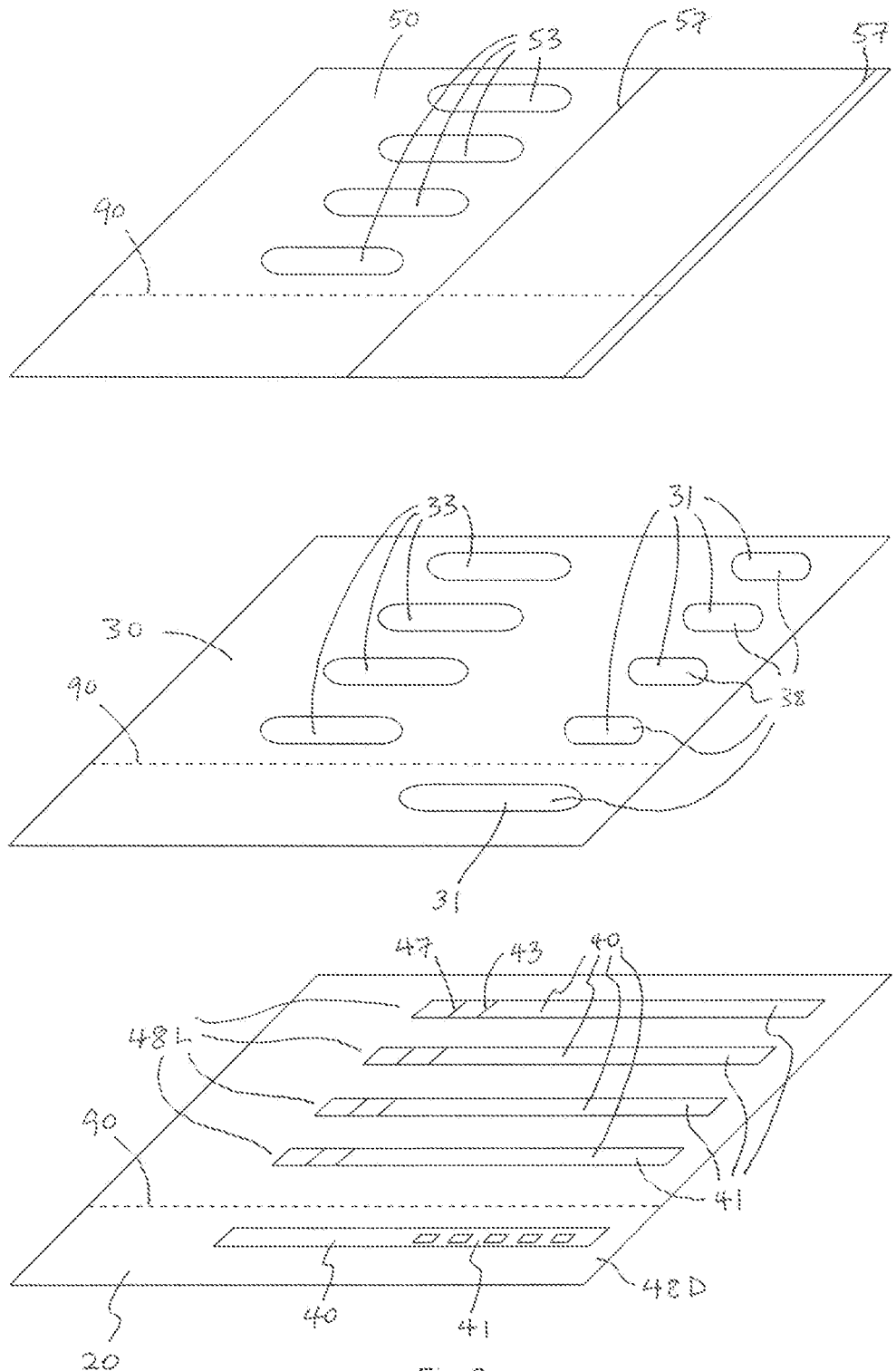
FIG. 8 is an exploded assembly illustration of the test kit of FIG. 7 before use.

In a fourth embodiment of the test kit 10 as shown in FIGS. 7 and 8, the test kit 10 comprises a plurality of test panels 48L, 48D each comprising a test strip 40 individually sealed between the base sheet 20 and the sealing sheet 30 before use of the test kit 10. Each test strip 40 has a sample collection portion 41, and the sealing sheet 30 has a corresponding plurality of sealed sample collection openings 31 before use of the test kit 10. Each sample collection opening 31 is similar to the sample collection opening 31 of the second embodiment shown in FIGS. 3 and 4, being configured to be opened to expose each sample collection portion 41 during use of the test kit by detaching the top sheet 50 from the sealing sheet 50. Each of the plurality of test panels 48L, 48D is configured to perform a different immunoassay. In this way, one test kit 10 can allow a number of different tests to be performed by providing multiple test panels 48 in a single convenient package. Each panel 48L, 48D may be configured similar to any one of the embodiments described above so that the plurality of test strips 40 may comprise any combination of lateral flow and/or dipstick test strips 40, depending on the tests that it is desired for the test kit 10 to comprise.

In the example of the fourth embodiment shown in FIGS. 7 and 8, the test kit 10 comprises four lateral flow test panels 48L and one dipstick test panel 48D. For added convenience, a line of perforations 90 is provided through the test kit 10 between the dipstick test panel 48D and its adjacent lateral flow test panel 48L to allow the dipstick test panel 48D to be manually separated from the test kit. This allows a user to collect the fluid analyte sample using the dipstick test panel 48D via a mid-stream collecting method without getting the fluid analyte sample onto the other test panels 48L.

It should be noted that in FIGS. 4, 6, and 8 where the lateral flow test strip 40 can be seen, the test lines 43 and control lines 47 are made visible only for illustration purposes as they are in fact invisible before use of the test kit 10.

For all embodiments, the base sheet 20, sealing sheet 30 and at least one top sheet 50 each preferably comprise a moisture barrier polymeric film so that the at least one test strip 40 is kept well sealed between the base sheet 20 and sealing sheet 30 before use of the test kit 10. In this way, the test kit 10 requires no additional moisture barrier packaging to keep the at least one test strip 40 stable during storage and transportation of the test kit 10 before use. This also greatly reduces the size of the test kit 10 and the space it takes up, which would have a significant impact particularly when test kits need to be moved in areas with poor transportation networks or accessibility. For example, a single healthcare worker going on foot to a remote location will be able to take with him or her a great many more of the test kits 10 of the present invention in a single hand-carry bag or case or even clothing pocket as compared to existing test kits with plastic cassettes in foil bags that would be significantly more bulky to carry. Doing away with the need for an additional moisture barrier foil bag and plastic cassette also significantly reduces the cost of the test kit 10 of the present invention, since each foil bag and each plastic cassette contributes to the total cost of each traditionally available test kit.

In addition, for all embodiments, the disposable test kit 10 of the present invention is preferably provided with at least one quick response (QR) code 80 on the test kit 10, more preferably located on the top sheet 50 for easy access. The at least one QR code 80 allows information such as manufacturing date, expiry date and source information of the at least one test strip 40 and the test kit 10 itself to be stored and retrieved, as well as allowing the test kit 10 to be associated or tagged with a single specific source of the fluid analyte. The specific source may be a patient or any other analyte supply, depending on the usage application of the test kit 10. The QR code is preferably located on a part 58 of the top sheet 50 where the part 58 of the top sheet 50 is never detached from the sealing sheet 30, or on a part of the sealing sheet 30 that is not overlayed by a top sheet 50 (depending on the configuration of the test kit 10). In this way, the quick response code 80 is never separated from the test strip 40 in the test kit 10 after use, and each test strip 40 can be correctly traced to its specific fluid analyte source.

For example, where the test kit 10 is used to diagnose presence of a disease in individuals of a large population of patients, having the quick response code 80 on each test kit 10 allows each test kit 10 to be indelibly and indubitably associated with only one specific patient, thereby minimizing or preventing mix-ups in test results from occurring. Where the test kit 10 has a panel form comprising multiple test panels, as described above in the fourth embodiment and as shown in FIG. 7, any test panel that is configured to be separable from the rest of the test kit 10 preferably has its own QR code to ensure that each and every test panel can be traced to a specific fluid analyte source.

As described in the various embodiments above, the present invention thus provides a low cost, low bulk disposable test kit 10 that can be easily associated with a specific analyte source or patient.

Whilst there has been described in the foregoing description exemplary embodiments of the present invention, it will be understood by those skilled in the technology concerned that many variations in details of design, construction and/or operation may be made without departing from the present invention. For example, where the test kit is configured to comprise multiple test panels, multiple lines of perforations 90 may be appropriately provided to allow one or more test panels to be separated from the test kit. While it has been described that the base sheet, sealing sheet and top sheet are preferably made of a moisture barrier polymeric film, they may alternatively be made of appropriately laminated paper with sufficient moisture barrier properties required for stable storage of the test strips therein. It is further envisaged that in various embodiments of the test kit, the top sheet may or may not be layered over all of the sealing sheet so long as it is layered over the sample collection opening to keep the sample collection opening sealed before use of the test kit.

The invention claimed is:

1. A disposable test kit comprising:
a base sheet;
a sealing sheet having at least one sealed sample collection opening before use of the test kit;
at least one test strip sealed between the base sheet and the sealing sheet before use of the test kit; and
at least one top sheet layered over the sealing sheet before use of the test kit to keep the at least one sample collection opening sealed, the at least one top sheet is at least partially detachable from the sealing sheet to open the at least one sample collection opening and expose a sample collection portion of the at least one test strip for receiving a fluid analyte thereon during use of the test kit.

2. The disposable test kit of claim 1, wherein the at least one sample collection opening and the sample collection portion allow the fluid analyte to be received by the sample collection portion via one of: a dipstick method, a drop method and a mid-stream collection method.

3. The disposable test kit of claim 1, wherein the sample collection opening is sealed by a cover before use of the test kit, the cover being attached to the top sheet such that at least partially detaching the top sheet from the sealing sheet detaches the cover from the sealing sheet to open the sample collection opening.

4. The disposable test kit of claim 1, wherein the at least one test strip is at least one of: a lateral flow test strip and a dipstick test strip.

5. The disposable test kit of claim 4, wherein the at least one test strip is at least one dipstick test strip and the sample collection portion comprises at least one test pad impregnated with a reagent.

6. The disposable test kit of claim 4, wherein the sealing sheet further comprises at least one transparent portion as a reaction window and wherein the at least one test strip is at least one lateral flow test strip having at least one test line viewable through the reaction window.

7. The disposable test kit of claim 6, wherein the at least one top sheet further comprises at least one transparent portion aligned with the reaction window of the sealing sheet.

8. The disposable test kit of claim 1, wherein the base sheet, the sealing sheet and the at least one top sheet each comprise a moisture barrier polymeric film.

9. The disposable test kit of claim 1, wherein the test kit requires no additional moisture barrier packaging to keep the at least one test strip stable during storage of the test kit before use.

10. The disposable test kit of claim 1, wherein the test kit comprises at least one quick response code provided thereon for storing information therein.

11. The disposable test kit of claim 1, wherein the at least one top sheet is reattachable to the sealing sheet to cover the at least one sample collection opening after use of the test kit to prevent the fluid analyte on the sample collection portion from coming into contact with another object.

12. The disposable test kit of claim 1, wherein the at least one top sheet comprises
a first top sheet layered over the sealing sheet to keep the sample collection opening sealed before use of the test kit, the first top sheet having a drop collection opening sealed before use of the test kit and
a second top sheet layered over the first top sheet to keep the drop collection opening sealed before use of the test kit,
wherein the first top sheet is at least partially detachable from the sealing sheet to open the sample collection opening of the sealing sheet and expose the sample collection portion of the test strip for receiving a fluid analyte thereon via one of: a dipstick method and a mid-stream collection method during use of the test kit, and
wherein the second top sheet is at least partially detachable from the first top sheet to open the drop collection opening on the first top sheet and expose the sample collection portion for receiving a fluid analyte thereon via a drop method during use of the test kit, thereby providing a user of the test kit with a choice of which of the first top sheet and the second top sheet to detach according to how the user prefers the fluid analyte to be received by the test kit.

13. The disposable test kit of claim 1, wherein the test kit comprises a plurality of test panels each comprising a test strip having a sample collection portion and individually sealed between the base sheet and the sealing sheet before use of the test kit, the sealing sheet having a plurality of sealed sample collection openings before use of the test kit, wherein each sample collection opening is openable by at least partially detaching the at least one top sheet from the sealing sheet to expose each sample collection portion during use of the test kit.

14. The disposable test kit of claim 13, wherein each of the plurality of test panels is performs a different immunoassay.

15. The disposable test kit of claim 13, wherein the test kit comprises at least one line of perforations provided therethrough and located between two adjacent test panels to allow at least one of the plurality of test panels to be manually separated from the test kit.

* * * * *